(12) United States Patent
Pelton (10) Patent No.: US 6,468,298 B1
(45) Date of Patent: Oct. 22, 2002

(54) GRIPPING DELIVERY SYSTEM FOR SELF-EXPANDING STENTS AND METHOD OF USING THE SAME

(75) Inventor: Brian L. Pelton, Menlo Park, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 84 days.

(21) Appl. No.: 09/752,715

(22) Filed: Dec. 28, 2000

(51) Int. Cl.[7] .......................... A61F 2/06; A61M 29/00
(52) U.S. Cl. ........................ 623/1.11; 606/198; 606/194
(58) Field of Search .................. 623/1.11; 606/198, 606/114, 113, 108, 194, 195

(56) References Cited

U.S. PATENT DOCUMENTS

| | | | |
|---|---|---|---|
| 6,123,712 A | | 9/2000 | Di Caprio et al. |
| 6,159,227 A | | 12/2000 | Di Caprio et al. |
| 6,319,259 B1 | * | 11/2001 | Lee et al. ............... 604/97.01 |
| 6,319,275 B1 | * | 11/2001 | Lashinski et al. ........... 606/108 |
| 6,322,586 B1 | * | 11/2001 | Monroe et al. ............. 606/108 |
| 6,325,814 B1 | * | 12/2001 | Euteneuer et al. .......... 606/108 |
| 2001/0016753 A1 | | 8/2001 | Caprio et al. |

* cited by examiner

Primary Examiner—David H. Willse
Assistant Examiner—Hieu Phan
(74) Attorney, Agent, or Firm—Fulwider Patton Lee & Utecht, LLP (57) ABSTRACT

A stent contracting apparatus configured with retractable grippers to engage the struts of a self-expanding stent to hold the stent in a collapsed position and to release the stent within a body lumen. The grippers of the stent contracting apparatus are moveable between a retracted and deployed position by an actuating mechanism which includes at least one control wire that extends outside the body lumen. A post-dilatation expandable member allows a physician to adjust the positioning of the expanded stent within the lumen if necessary.

28 Claims, 4 Drawing Sheets

GRIPPING DELIVERY SYSTEM FOR SELF-EXPANDING STENTS AND METHOD OF USING THE SAME

BACKGROUND OF THE INVENTION

The present invention relates to the field of delivery systems and methods for deploying intravascular stents, and more specifically, to delivery systems that incorporate mechanical gripping devices for maintaining self-expanding stents in a compressed state during delivery to facilitate accurate deployment of the stent within the body vessel.

Cardiovascular disease currently takes the lives of almost one million Americans each year. Diseases of the vascular system may occur as a result of several etiologies that lead to the development of atherosclerosis, a disease of the arteries characterized by thickening, loss of elasticity, and calcification of arterial walls, which manifests itself in two predominant forms. In one form, a narrowing of blood vessels impedes blood flow through the vessel lumen. In another form, arterial walls degenerate due to the formation of aneurisms, which cause the walls of the affected artery to weaken and balloon outward while thinning. Although many patients with vascular disease choose to explore treatments that do not require surgery, such as cholesterol reducing regimens or drugs, beta blockers to regulate and reduce blood pressure, and blood-thinning agents, vascular surgery still remains an often performed procedure. In the United States alone, more than 850,000 angioplasties and bypasses are currently performed annually at a cost of around $30 billion.

As a less invasive alternative to bypass surgery, atherectomy has become a widely accepted procedure because it removes built up plaque from the inside of blood vessels that have experienced the progressive occlusive effects of atheroscierosois. Atherectomy is exercised most commonly in major arterial vessels, such as the coronary arteries, and can be accomplished by various means, including lasers, incisions, drill tip catheters. Angioplasty is another non-invasive procedure where a balloon-tipped catheter or other device is used to enlarge a narrowing in a artery. This enlargement is accomplished by radially compressing the atherosclerotic plaque of a stenosis against the inside of the artery wall, and dilating the lumen of the artery.

Although angioplasty procedures are widely accepted for treatment of occluded arteries, the problem of restenosis following an angioplasty treatment is a significant danger that a patient must face. Restenosis is the closure of an artery following trauma caused by attempts to open an occluded portion of the artery, and is frequently caused by the elastic rebound of the arterial wall and/or by dissections in the vessel wall caused by the angioplasty procedure. To combat restenosis, vascular surgeons implant tubular supports known as "stents" into surgically repaired vessels.

Stents are used to support dissections in vessel walls and to prevent the elastic rebound of repaired vessels, thereby reducing the level of restenosis for many patients. The stent is typically inserted by catheter into a vascular lumen at an easily accessible location, such as the brachial or femoral arteries, and then is advanced through the vasculature to the deployment site. The stent is initially maintained in a radially compressed or collapsed state to enable it to be maneuvered through the body lumen. Once in position, the stent is expanded into contact with the diseased portion of the arterial wall, thereby providing internal support for the lumen. One method for expanding the stent at the site of the stenosis employs some active external means to apply a controlled force that expands the stent, such as a balloon in typical balloon angioplasty catheter. Details of prior art expandable stents and their representative associated delivery systems can be found in U.S. Pat. No. 3,868,956 (Alfidi et al.); U.S. Pat. No. 4,512,1338 (Balko et al.); U.S. Pat. No. 4,553,545 (Maass, et al.); U.S. Pat. No. 4,733,665 (Palmaz); U.S. Pat. No. 4,762,128 (Rosenbluth); U.S. Pat. No. 4,800,882 (Gianturco); U.S. Pat. No. 4,886,062 (Wiktor); U.S. Pat. No. 5,514,154 (Lau, et al.); U.S. Pat. No. 5,421,955 (Lau et al.); U.S. Pat. No. 5,603,721 (Lau et al.); U.S. Pat. No. 4,655,772 (Wallsten); U.S. Pat. No. 4,739,762 (Palmaz); U.S. Pat. No. 5,569,295 (Lam); U.S. Pat. No. 5,899,935 (Ding); U.S. Pat. No. 6,007,543 (Ellis et al.); U.S. Pat. No. 6,027,510 (Alt); and U.S. Pat. No. 6,077,273 (Euteneuer et al.).

Another method employed for expansion of a stent at the site of stenosis relies on the removal of some restraint that holds the stent in a compressed state, such as a sheath, a collar, a clamp, or a membrane. For this method to succeed, the stent must be capable of self-expansion when the restraint is removed. Self-expanding stents can be formed from shape memory metals or super-elastic nickel-titanium (NiTi) alloys (nitinol), which will automatically expand from a compressed state when the stent is advanced out of the distal end of the delivery catheter into blood vessel once its restraining device is removed. Self-expanding stents, manufactured from expandable heat-sensitive materials, allow for phase transformations of the material to occur, resulting in the expansion and contraction of the stent.

Details of prior art self-expanding stents and their representative associated delivery systems can be found in U.S. Pat. No. 4,580,568 (Gianturco); U.S. Pat. No. 4,655,771 (Wallsten); U.S. Pat. No. 4,655,771; U.S. Pat. No. 4,732,152 (Wallsten); U.S. Pat. No. 4,848,343 (Wallsten); U.S. Pat. No. 4,830,003 (Wolff, et al.); U.S. Pat. No. 4,875,480 (Imbert); U.S. Pat. No. 4,913,141 (Hillstead); U.S. Pat. No. 4,950,227 (Savin); U.S. Pat. No. 5,071,407 (Terrain); U.S. Pat. No. 5,064,435 (Porter); U.S. Pat. No. 5,571,135 (Fraser); and U.S. Pat. No. 5,989,280 (Euteneuer et al.).

A need exists in the market place for a self-expanding stent delivery system that is effective to maintain the stent to its low profile state and allow for accurate and reliable placement within the vessel lumen at the deployment site. Such a system also should be easy to maneuver and control for the physician performing the procedure. The surgeon deploying the stent would also benefit if such a system was designed with an adjustment element to allow for quick and accurate alignment of a post-dilatation stent in the event of an inaccurate placement of the stent.

Various attempts have been made to develop delivery systems for self-expanding stents that result in accurate and reliable deployment in the vessel lumen, however, there have been some problems associated with these systems. Many incorporate delivery sheaths to restrain the stent prior to deployment. Such devices typically add to the profile of the stent delivery catheter thereby adding a possible obstacle to placement in a narrow body lumen. Often, the stent itself is not compressed to a small enough diameter to adequately navigate the tortuous vasculature of the anatomy, which can result in damage to vessel walls and inefficient delivery.

Deployment systems for self-expanding stents may also imprecisely deploy the stent due to a failure to compensate for axial energy storage in the stent itself, or frictional forces created by the delivery system. For example, systems that rely on a "push-pull" design can experience movement of the collapsed stent within the body vessel when the sheath and inner catheter are pushed together. Additionally, some self-expanding stents can store energy axially from the frictional force generated as the outer restraining sheath is retracted over the expanding stent. This can cause the stent to act somewhat like a spring, storing energy as the frictional force acts on the stent. As the stent expands beyond the end of the sheath, stored energy can be immediately released, which can cause the stent to "jump" or move from the desired position, resulting in inaccurate placement in the body vessel.

Additionally, some delivery systems fail to provide an element to permit adjustment of the post-dilatation positioning of the stent within the vessel in the event of an imprecise deployment. In these circumstances, surgeons must adjust the positioning of the stent by removing the initial delivery system and inserting a second delivery catheter to reposition the stent. This procedure can be both time consuming and costly to the patient.

Therefore, there is a need for a self-expanding stent delivery system that reliably maintains the collapsed stent in a low delivery profile, facilitates minimal movement of the stent during deployment, results in reliable accurate positioning within the vessel lumen, and incorporates a post-dilatation device for adjusting the stent after deployment if required. The present invention satisfies these and other needs.

SUMMARY OF THE INVENTION

The present invention provides a delivery system for a self-expanding stent that maintains the compressed stent in a low delivery profile for navigation of the vasculature and increases the reliability and accuracy of deployment at the target site within the body lumen. Moreover, the present invention overcomes the shortcoming of some traditional restraining delivery systems which require a sheath to maintain the collapsed stent in its delivery position and also reduces the tendency of the stent to release stored energy that may cause it to "jump" in the distal direction, as its proximal end exits the sheath. The present delivery system achieves the above-described advantages by utilizing a mechanically controlled apparatus which contracts the self-expanding stent and secures the stent in a low profile configuration during delivery.

The delivery system of the present invention is characterized by a stent contracting apparatus which coaxially receives the stent and has retractable grippers (also referred to herein as "grippers") selectively extendable to hook onto the stent and draw the stent radially inwardly into its low profile delivery configuration. The system includes an actuator operable to release the grippers from the stent to free it for expansion. In one aspect of the invention, the actuator is operable to cause the grippers to progressively release the stent, progressing from the distal end of the stent to the proximal end.

In another aspect of the present invention, radial grippers are connected on their inner extremities to longitudinal rails which are shiftable longitudinally in one direction to selectively pivot the grippers to their retracted positions to hook the walls of the stent and to hold it in its compressed delivery profile. The grippers also are shiftable in the opposite direction to unhook their respective free ends from the retained stent to free the stent for expansion within the patient's vasculature.

In preparation, the stent contracting apparatus may be telescopically advanced into the inner lumen of the expanded stent with the compressed grippers hooked to the struts of the stent to hold the stent. Then, the grippers can be actuated to compress the stent to a low profile for delivery within the patient's vasculature.

In a particular aspect of the present invention, the radial grippers become progressively shorter in length, from the distal to the proximal end of the stent contracting apparatus, to provide a progressive and controlled release and expansion of the stent from its compressed position to enhance accurate placement within the vasculature.

A post-dilatation expandable balloon may be attached proximal to the stent contracting apparatus to facilitate adjustment of the position of the expanded stent in a post-dilation procedure. The grippers of the stent contracting apparatus may be retracted and the apparatus advanced distally beyond the expanded stent to position the balloon longitudinally within the expanded stent. The balloon may be inflated, as needed, to distend against the stent wall to adjust the stent placement as necessary.

Other objects and features of the invention will become apparent from consideration of the following descriptions, taken in conjunction with the accompanying drawings, which illustrate by way of example the features of the invention.

DETAILED DESCRIPTION OF THE PREFERRED EMBODIMENTS

Figure 1:
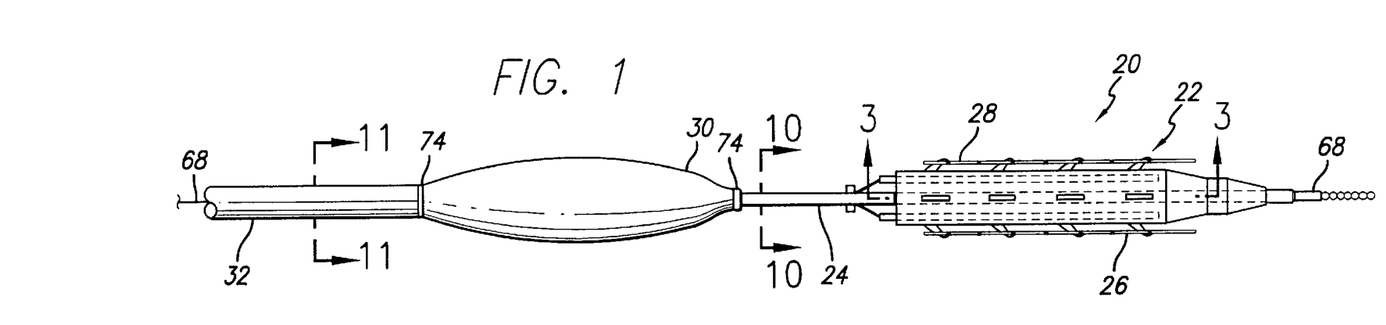
FIG. 1 is a longitudinal sectional view of a composite stent delivery system made in accordance with the present invention wherein the sent contracting apparatus and expandable member are in their expanded positions.
Figure 3:
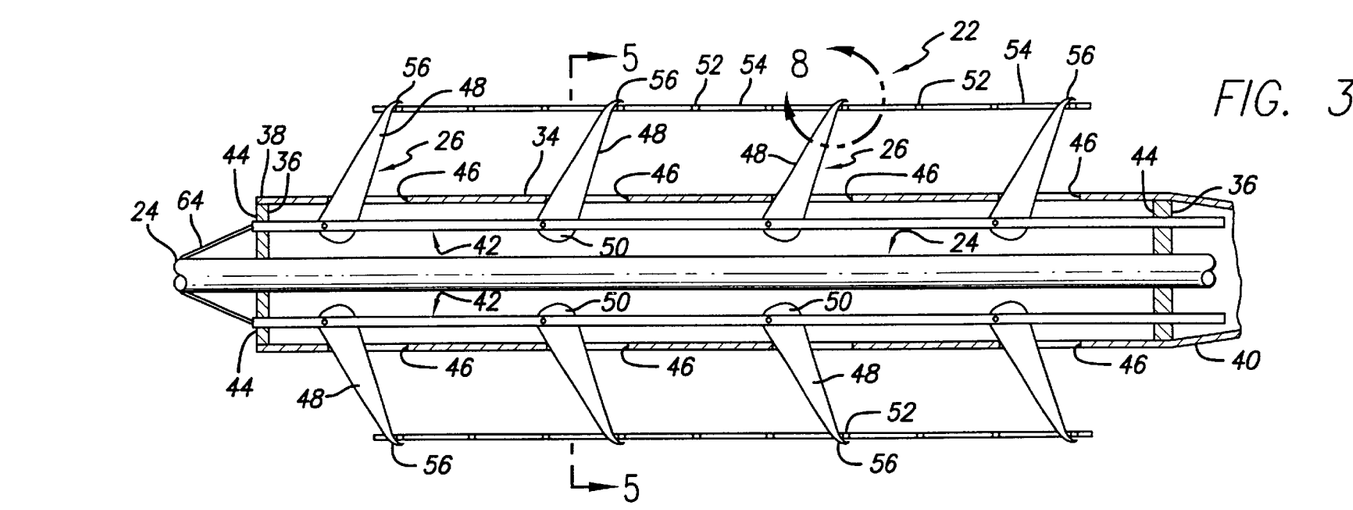
FIG. 3 is a longitudinal sectional view taken along line 3—3 of FIG. 1.
Figure 4:
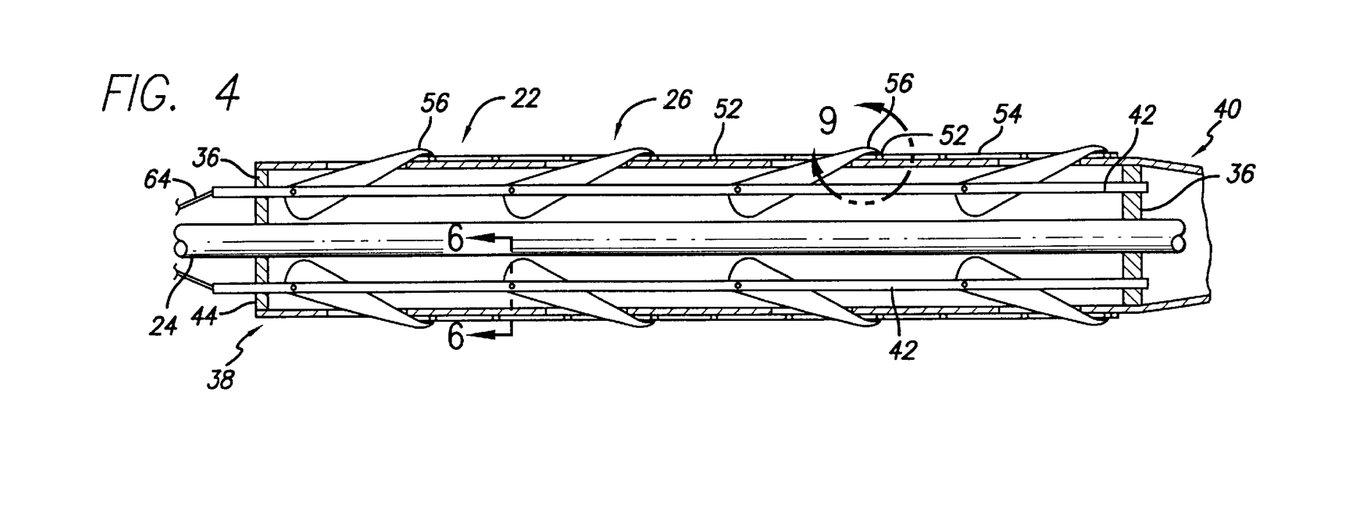
FIG. 4 is a longitudinal sectional view, similar to FIG. 3, but shown with the stent contracting apparatus in its collapsed position and holding the stent in its collapsed position.

Turning now to the drawings, in which like reference numerals represent like or corresponding elements in the drawings, and initially to FIGS. 1, 3 and 4, the present invention is embodied in a stent delivery system 20 that includes, generally, a stent contracting apparatus 22 mounted to the distal extremity of an inner tubular member 24. The stent contracting apparatus 22 is made up of numerous cantiliverally mounted, pivoting retractable grippers 26 (also referred to herein as grippers) which are selectively shiftable between the respective radially outwardly deployed position (shown in FIG. 3) and a contracted position (shown in FIG. 4) for collapsing and holding a self-expanding stent 28 in its reduced profile for deployment in a patient's vascular system. Stent delivery system 20 further includes an expandable member 30 which can be used for post-expansion of the stent 28 after the stent has been deployed in the patient's vasculature. Expandable member 30 is mounted on a tubular member 32 which extends to a location outside of the patient where a control handle (not shown) is attached to the tubular member 32. The distal end of the expandable member 30 is, in turn, attached to the inner tubular member 24 to create continuous inner lumens which are utilized for receiving control wires and a guide wire which will be described in greater detail below.

The stent contracting apparatus 22 includes an outer tubular member 34 forming a rigid housing fixedly mounted to the inner tubular member 24 by mounting disks 36 located at the proximal and distal ends 38 and 40 of the outer tubular member 34. The stent contracting apparatus 22 further includes actuating rails 42 projecting substantially parallel to the axis of the inner tubular member 24. These activating rails 42 extend through openings 44 located in the mounting disks 36 to permit limited axial movement therethrough. Longitudinal gripper apertures 46 are spaced annularly equidistant about the outer tubular member 34 to allow the free extremities 48 of the finger grippers 26 to pass radially therethrough. The mounting ends 50 of the finger grippers 26 are pivotly attached to the actuating rails 42. In the embodiment shown and described herein, the inward and outward motion of the grippers 26 is controlled by the longitudinal advancement and retraction of the actuating rails 42.

The inner tubular member 24 and proximal tubular member 32 are sufficient length to be threaded through the patient's vasculature from the access site, for instance, in the groin area, to a stenotic region in the coronary arteries, carotid arteries or peripheral locations. The inner tubular member 24 must be composed of a material sufficient in strength to support the mounted stent contracting apparatus 22, while being flexible enough to negotiate the patient's often tortuous vasculature.

Figure 2:
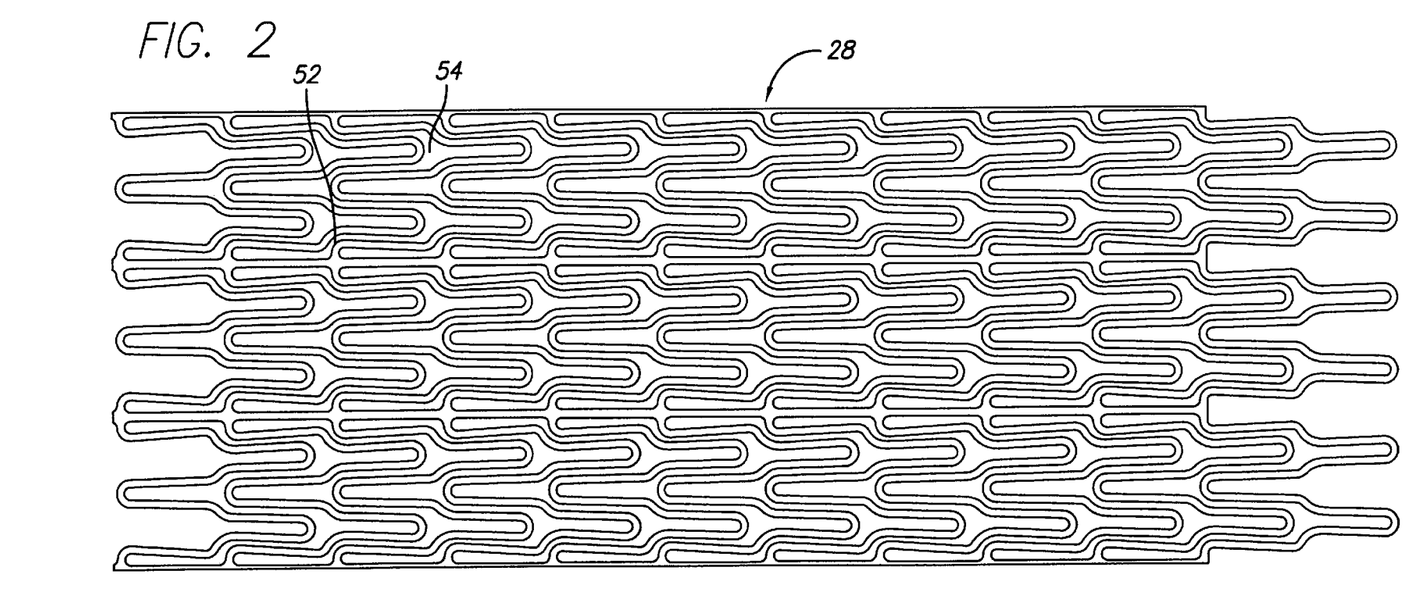
FIG. 2 is a plan view, in enlarged scale, of a flattened section of the self-expanding stent shown in FIG. 1.

The stent contracting apparatus 22 of the present invention may be utilized to deploy a conventional self-expanding stent 28 (FIGS. 1 and 2) which is typically made of a series of struts 52 which undulate back and forth and are formed along their tubular periphery with openings 54. It should be appreciated that the self-expanding stent 28 disclosed herein is just one of a number of many different self-expanding stent designs which can be utilized in accordance with the present invention.

The stent contracting apparatus 22 may be of any desirable configuration for insertion telescopically into the open end of the self-expanding stent 28, and the grippers 26 are formed with respective hooks 56 to grip the struts of the stent and hold it collapsed radially inwardly to the low delivery profile shown in FIG. 3. These hooks 56 are designed to extend between the openings 54 in the stent 28 to grip and hold a strut 52.

Figure 5:
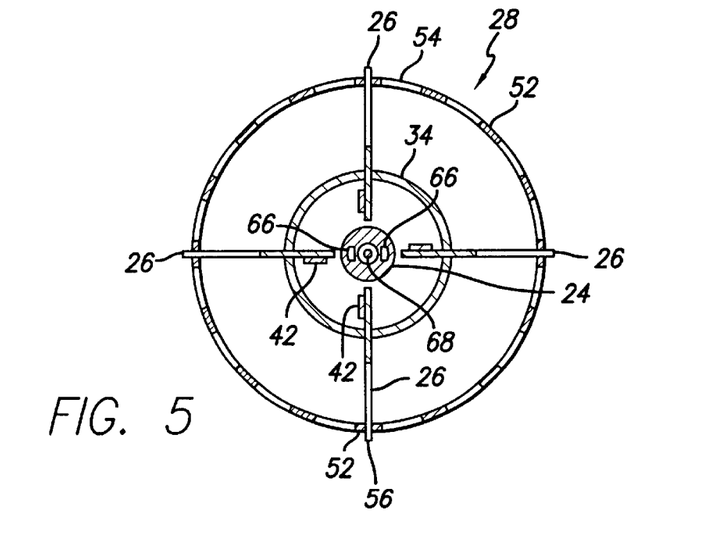
FIG. 5 is a transverse sectional view taken along line 5—5 of FIG. 4.

By way of example, FIG. 3 depicts the stent contracting apparatus of the present invention with the outer tubular member 34 formed such that the gripper apertures 46 are positioned and configured to capture the free extremities 48 of each gripper 26 with the distal and proximal edges 58 and 60 acting as deployment and cam edges (FIGS. 3 and 4). In the embodiment shown and described herein, four actuating rails 42 are annularly arrayed in respective quadrants about the inner tubular member 24 as shown in FIG. 5, within the lumen of the outer tubular member 34. The individual actuating rails 42 are located on diametrically opposite sides of the inner tubular member 24, and spaced evenly thereabout.

Figure 6:
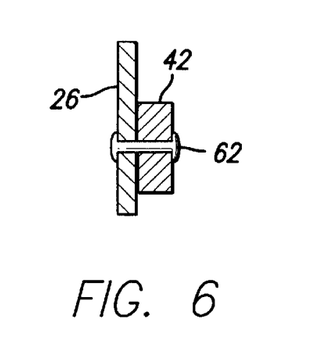
FIG. 6 is a transverse sectional view, in enlarged scale, taken along line 6—6 of FIG. 3.

In the particular embodiment disclosed herein, the grippers 26 are mounted on the actuating rails 42 using pivot pins 62 (FIG. 6), or similar fastening devices, to allow free rotation thereon. As viewed in FIG. 4, each gripper 26 is configured on its distal edge 58 and proximal edge 60 with a sliding surface arranged to selectively abut against the distal and proximal edges of the gripper aperture 46, which serves as a cam surface to move each gripper 26 into the contracted and expanded positions. The edges 58 and 60 of each gripper 26 can be coated with low friction material, such as Teflon®, to slide freely over any strut 52 and avoid damage thereto. Alternatively, polymeric material can be utilized to form the grippers 28 which should also maintain low frictional contact with the struts of the stent. Other suitable materials for the grippers include stainless steel, nitinol, and other biocompatible materials having sufficient material strength to maintain the self-expanding stent in a collapsed or compressed position during delivery.

It will be appreciated that in practice, the inner tubular member 24 can be made from flexible tubular materials, such as polyethereketone (PEEK), or similar material, having excellent compressive strength yet being reasonably flexible. Other elements of the stent delivery system 20, such as the expandable member 30, proximal tubular member 32, and be constructed with similar components to conventional catheter systems used for angioplasty procedures and may be made of suitable polymers, such as polyethylene, polyester, polyamide and the like which are currently being used and known to those skilled in the art. It should also be appreciated that although the inner tubular member 24 is shown as a separate piece from the proximal tubular member 32, it is possible to utilize a single piece of tubular material to create a composite device. In this manner, the expandable member 30 can be simply mounted on the surface of a continuous tubular member and can be in fluid communication with an additional lumen formed in the tubular member.

Figure 7:
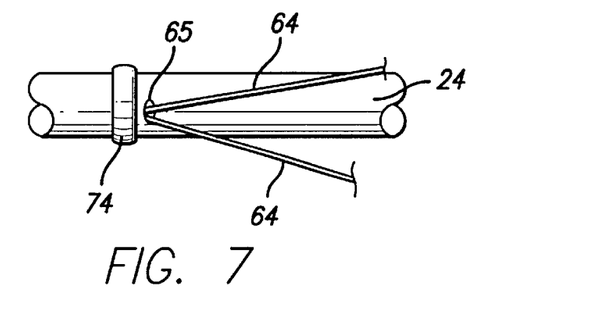
FIG. 7 is a longitudinal section view, in reduced scale, of the stent contracting apparatus shown in FIG. 3.

As shown in FIGS. 3 and 4, the outer tubular member may be affixed directly to the inner tubular member 24. The proximal ends of each sliding actuator rail 42 are connected to small gauge control wires 64 which can be threaded through control wire slots 65 (FIG. 7) located in the wall of the inner tubular member 24. These control wires 64 may be twisted together to project proximally through a control wire lumen 66 extending through the inner tubular member 24 to a proximal control handle (not shown). In addition, there may be more than one control wire lumen 66 to receive the control wires 64. The proximal control handle can be equipped with a locking mechanism (not shown) to lock the grippers 26 in their contracted position to maintain the stent 28 in its compressed delivery position. These control wires 64 can be about 0.0006 inches in diameter and must possess sufficient strength to push and pull the sliding actuating rails 42 to deploy and contract the grippers 26. In practice, biasing springs (not shown) may be incorporated within the stent contracting apparatus 22 to urge the actuating rails 42 distally to maintain the grippers 26 in the expanded position until the system is ready to compress and deliver a stent. The handle and locking mechanism could be used to position the grippers 26 within the lumen of the stent so that the hooks 56 can engage the struts of the stent. The handle can then be actuated to compress the stent, via the action of each gripper.

The composite stent delivery system could be co-axially mounted on a guide wire 68 which helps deliver the stent system to the desired treatment area. The guide wire 68 extends through a guide wire lumen 67 which extends along the entire length of the proximal tubular member 32 and inner tubular member 24. The stent delivery system as shown herein is described in conjunction with an over-the-wire system, however, the stent delivery system can be easily modified to utilize rapid exchange features well-known in the art. Additionally, the stent delivery system of the present invention is applicable to both coronary and peripheral applications and can be used in a number of different body lumens which require the placement of a stent device. The gripping apparatus and expandable member can be made to support current and future lines of arterial stents, ranging from about 2.0 to 8.0+mm in diameter and about 8 to 50 mm in length.

Referring back to FIG. 1, the stent delivery system 20 includes a post-expandable member 30 mounted on the proximal inner tubular member 32 which is proximal to the stent contracting apparatus 22. This expandable member 30 is in fluid communication with an internal inflation conduit 72 which extends proximally from the control handle. The post dilatation expandable member 30 will allow for touch-up work in a timely manner if the stent 28 is not optimally deployed, eliminating the need for a second balloon expandable catheter.

It will be appreciated that the delivery system of the present invention may be prepared in advance of a dilatation procedure by telescopically advancing the stent contracting apparatus 22, with its grippers in a radially outwardly rotated deployed position, into the inner diameter of a self-expanding stent 28 in its expanded position so that the two elements are longitudinally aligned. The finger grippers 26 can then be extended into the openings 54 of the stent so that the hooks 56 extend upward and over the struts 52 of the stent. The grippers 26 can be actuated upwards by the stent contracting apparatus. Additionally, the stent may be compressed by an external compression apparatus (not shown) around the deployed finger grippers 26, such that the grippers 26 project radially outwardly through the longitudinal openings 54 in the stent structure.

The stent contracting apparatus 22 may be prepared by drawing the actuator wires proximally relative to the inner tubular member 24 to draw the actuator control rails 42 proximally to the position shown in FIG. 4. As shown in FIG. 3 in general and in FIGS. 8 and 9 in detail, the proximal travel of the rails 42 relative to the tubular member 24 and outer tubular wall 34 will draw the transverse pivot pins 62 proximally, thereby translating the proximal edges 60 of the respective finger grippers 26 to engage the edge of the gripper openings 46. The free end of the grippers defining the hook 56 will be rotated distally and radially inwardly to the position shown in FIG. 4.

Figure 8:
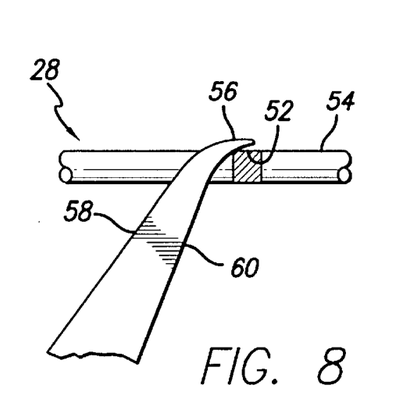
FIG. 8 is a detail view, in enlarged scale, taken from the circle designated 8 in FIG. 4.

The delivery system may then be prepared by advancing the stent contracting apparatus 22, with its grippers 26 retracted so that it is inserted within the inner diameter of a self-expanding stent 28. Then, the control wires 64 may be advanced distally to translate the actuating rails 42 distally relative to the inner tubular member 24 and the outer tubular member 34. The hooks 56 of the free extremities of the grippers may be aligned with the openings 54 between the struts 52 of the stent 28 to be projected radially outwardly therethrough, thus aligning the respective hooks with a strut 52 as shown in FIG. 8.

Figure 9:
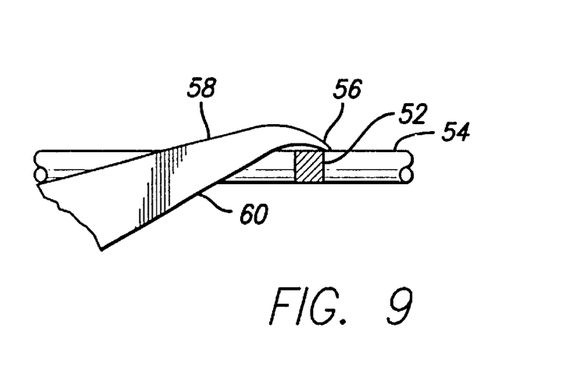
FIG. 9 is a detail view, in enlarged scale, taken from the circle designated 9 in FIG. 3.
Figure 10:
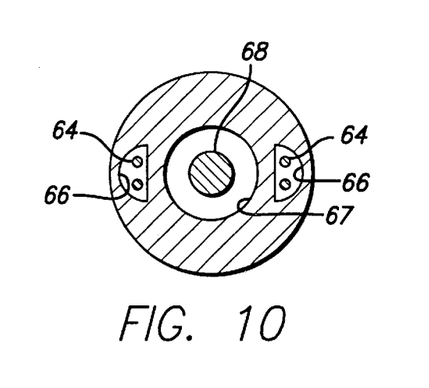
FIG. 10 is a cross-sectional view taken along line 10—10 of FIG. 1.
Figure 11:
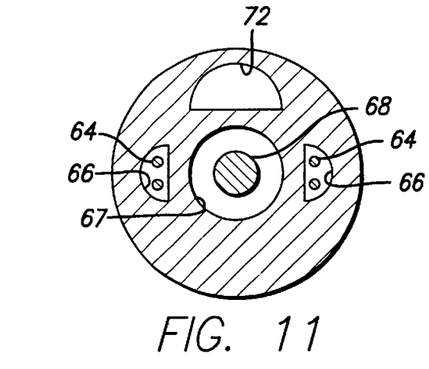
FIG. 11 is a cross-sectional view taken along line 11—11 of FIG. 1.

The stent itself then may be contracted in a conventional manner so that the grippers 26 project through the openings of the stent 28 and are then free to rotate radially inwardly when their respective rails 42 are translated proximally. As shown in FIGS. 8 and 9, after the stent 28 is compressed, the rails 42 are retracted proximally thereby fully rotating radially inward the grippers 26 to their contracted position around the compressed stent 28 such that the hooks 56 secure a stent strut 52. The grippers 26 are then locked in their contracted position as shown in FIG. 4 to hold the stent 28 ready until it is to be used for an implant procedure. It will be appreciated that the patient to be treated with the self-expanding stent will be prepped in the normal manner and access to the vascular system will be achieved, as for example, via the femoral artery. The access may be had by advancing the guide wire 68 to the desired region in a conventional manner. The entire system may be advanced through a guide catheter to a location near the stent implantation site. It will be appreciated that one or more opaque markers 74 (FIG. 1) may be mounted on the apparatus 22 to enhance fluoroscopic viewing during navigation to the stent site.

Once the stent contracting apparatus 22 has been positioned within the stent site, the physician may grasp the handle proximal end of the inner tubular member 24 to unlock, then advance the control wires 64 and, consequently, the actuator rails 42 to translate them distally thereby shifting the spacial relationship of the gripper actuator apertures to positions generally radially and outwardly from their respective pivot pins, thereby freeing the respective grippers to rotate radially outwardly. In some instances, the radially outwardly movement of the free extremities of the respective grippers may be assisted by engagement of the respective deployment cams with the deployment slider surfaces on the radially inner sides of the respective grippers 26 (See FIG. 3). The radially outwardly deployment of the grippers 26 from their contracted position around the compressed stent 28 allows the stent to gradually expand within the vessel lumen with the radially outwardly rotation of the grippers 26. This can be achieved at a carefully controlled rate.

It will be appreciated that the stent 28 will be positioned with the body lumen in the desired location. When the stent is positioned within the body lumen, it is possible that one or more of the hooks 56 may remain engaged with the struts 52 which may cause the hook 56 to wedge between the strut and the wall of the body lumen. In such a case, the hook 56 will not freely release from the stent. In such an occurrence, it is possible for the physician to push the control wires 64 distally to rotate the free extremity 48 of the grippers 26 counter clockwise to help release the hooks 56 from the struts of the stent. Once the hooks have been released from the strut, the entire contracting apparatus 22 can be disengaged from the stent and locked into its retracted position, allowing the physician to withdraw the entire system 20 from the patient's vasculature. If the stent is still not fully deployed, the physician can then utilize the expandable member 30 by replacing it into the inner diameter of the expanded stent and inflated to adjust the expansion of the stent to the vessel wall. After the stent has been adjusted, the entire stent delivery system 20 may be then withdrawn from the patient's vasculature.

Figure 12:
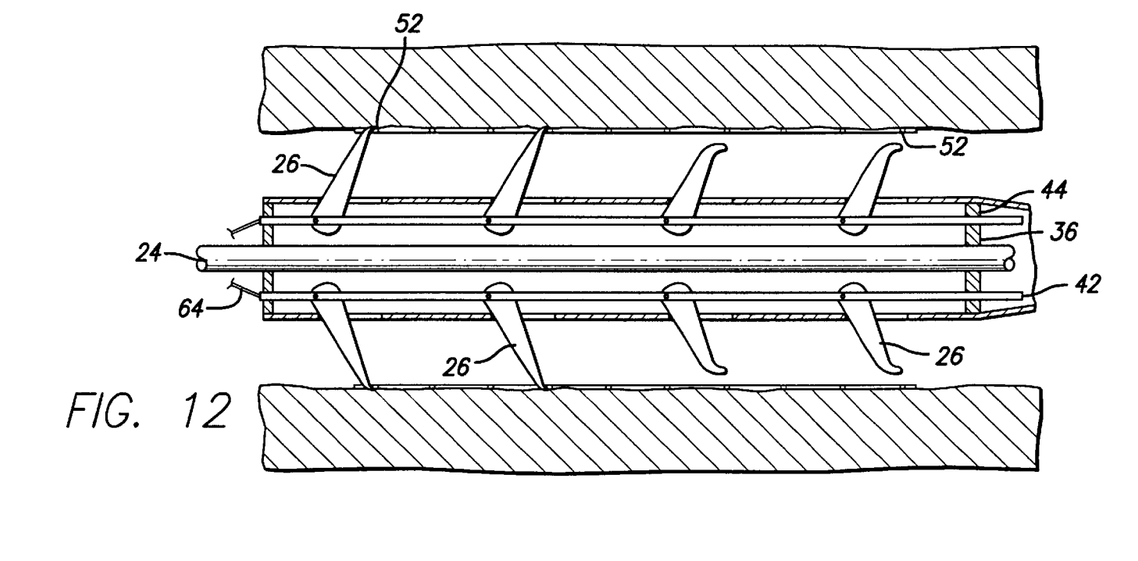
FIG. 12 is a longitudinal sectional view of the stent contracting apparatus similar to FIG. 4, wherein the stent contracting apparatus is within a vessel lumen deploying a stent.

Referring now to FIG. 12, the grippers 26 can be constructed to, during release from the stent 28, progressively unhook the distal to the proximate end of the expanding stent. In this manner, the physician will first release the distal extremity of the stent allowing it to expand only in its distal portion allowing the physician to observe how the stent deploys and to identify the correct location thereof. This advantage may be obtained by constructing the grippers 26 such that they are progressively shorter in length as they approach the distal end of the contractor apparatus 22, as is shown in FIG. 12. To this end, it will be appreciated that the grippers 26 may be shaped and configured such that the more distal grippers can be shorter than the proximal grippers to allow the hooks 56 at the free ends of the more distal grippers to initially disengage the distal extremity of the stent, allowing the distal portion of the stent to fully expand. The remaining portion of the stent can progressively continue its release of the stent along its longitudinal length until the most proximal grippers completely release the stent. It should also be appreciated that the proximal end of the stent could be released earlier than the distal end, if desired. In this manner, the shorter grippers 26 would be located at the proximal end of the stent contracting apparatus 22. It should also be appreciated that different configurations and sizes of grippers 26 can be utilized to achieve the desired mode of expansion of the stent. Therefore, various other combinations of shorter and longer retractable grippers 26 can be utilized in accordance with the present invention.

It should also be appreciated to those skilled in the art that the components of the stent contracting apparatus 22 may be relatively short to provide a minimum extent of body motion lengthwise in the vasculature. It is important that the rails 42 and inner tubular member 24 have sufficient column strength to provide for longitudinal translation forces sufficient to drive the pivotally attached ends of the grippers 26 distally for deployment and that the grippers themselves have sufficient resistance to bending to hold the stent in the contracted position as is shown in FIG. 4.

It will be appreciated that the stent contracting apparatus 22 of the present invention may take many different forms. As an example, the grippers could be in the form of resilient leaf springs with cantileverly mounted leaf springs with the distal hook ends threaded radially outwardly through apertures comparable to the gripper aperture 46. Longitudinal shifting would cause the leaf springs to be projected radially outward to hook the struts of the stent and to then be drawing curvalinearly back into a housing comparable to the outer tubular member 34 to draw the stent radially inwardly to its low profile configuration. In some applications, as for example, where the expanse from the access site to the implant site is relatively short, a rotary actuator system may be employed whereby one or more wires, similar to the control wires 64, may be rotated on their axes by crank handles to rotate an actuating mechanism relative to a cage or housing to cause leaf spring grippers to thread outwardly to form apertures which hook the stent and, with the rotation reversed, draw the stent radially inwardly to its low profile orientation.

From the foregoing, it will be appreciated that the stent contracting apparatus of the present invention allows for a very low delivery profile for a compressed self-expanding stent, and securely maintains the stent in a uniformly compressed state throughout its delivery through the vasculature, thereby providing surgeons with a reliable and durable stent delivery system. Further, the progressive and controlled deployment of the grippers results in an evenly expanded and accurately placed stent at the delivery site. Finally, because the post-dilatation balloon is readily available to the surgeon if adjustment of the expanded stent placement is required, the previous time consuming and costly reliance on withdrawal of the delivery catheter and insertion of a balloon dilatation catheter is no longer required.

While a particular form of the invention has been illustrated and described, it will also be apparent to those skilled in the art that various modifications and changes can be made with regard to the foregoing detailed descriptions without departing from the spirit and scope of the invention. More specifically, the stent contracting apparatus of the present invention is not limited for use with any particular type of actuation design or self expanding stent configuration, and is not limited to any specific type of vascular application. It will also be appreciated that the proximal end of the catheter system may be formed with various controls and handles to facilitate manipulation of the actuator system. Moreover, the post-dilatation expandable member may be expanded by any number of well known techniques. Accordingly, it is not intended that the invention be limited except by the appended claims.

What is claimed is:

1. A stent contracting apparatus for maintaining a self-expanding stent in a collapsed delivery position for implantation in a body lumen, comprising:

a plurality of retractable grippers moveable between a retracted position and a deployed position, each retractable gripper having a hook-like projection adapted to engage a strut of the stent to maintain the stent in a collapsed position when the retractable grippers are in the retracted position; and an actuating mechanism associated with each retractable gripper for moving the retractable grippers between the retracted and deployed positions;

wherein the retractable grippers disengage from the struts of the stent when placed in the deployed position.

2. The stent contracting apparatus of claim 1, wherein:

the retractable grippers progressively release the struts of the stent as the grippers are moved into the deployed position.

3. The stent contracting apparatus of claim 2, wherein:

the stent has a distal region and a proximal region and the retractable grippers progressively release the struts in the distal region of the stent for expansion prior to the release of the struts located in the proximal region of the stent.

4. The stent contracting apparatus of claim 1, wherein:

the actuating mechanism includes a plurality of actuating rails, each retractable gripper being pivotally mounted to one of the actuating rails, the actuating rails being moveable to move the retractable grippers between the retracted and deployed positions.

5. The stent contracting apparatus of claim 4, further including:

a housing for holding the plurality of retractable grippers and actuating rails, the housing including a plurality of apertures through which the hooklike projection of each retractable gripper extends radially outward therethrough.

6. The stent contracting apparatus of claim 5, wherein:

the housing is an outer tubular member having a distal end and a proximal end with a mounting disk located at each of the distal and proximal ends;

the retractable grippers being spaced longtitudinally along the outer tubular member apart from one another to engage the struts of the stent when the grippers are placed in their retracted position, the mounting disks having openings extending therein for receiving the actuating rails which allow the actuating rails to move longitudinally along the length of the outer tubular member to move the retractable grippers between the retracted and deployed positions.

7. The stent contracting apparatus of claim 6, wherein:
each actuating rail is attached to a control wire which extends to a proximal location outside of the body lumen for selectively moving the rails longitudinally along the tubular member to move the retractable gripper between the retracted and deployed positions.

8. The stent contracting apparatus of claim 7, further including:
an inner tubular member having a proximal end and a distal end while the distal end, wherein the outer tubular member forming the housing is mounted coaxially over the inner tubular member near the distal end; and
the inner tubular member has a lumen extending therethrough for receiving the control wires.

9. The stent contracting apparatus of claim 1, wherein:
the stent includes a plurality openings between the struts forming the stent and the hook-like projections of each retractable gripper is adapted to extend through an opening of the stent to engage the strut of the stent.

10. The stent contracting apparatus of claim 2, wherein:
each retractable gripper has a specific length and the retractable grippers are aligned such that the retractable grippers having a shorter length than an adjacent retractable gripper will disengage the strut of the stent prior to the longer adjacent retractable gripper.

11. The stent contracting apparatus of claim 8, further including:
a second lumen extending through the inner tubular member for receiving some of the control wires.

12. The stent contracting appparatus of claim 1, wherein:
the retractable are arranged in four rows, each row having at least four retractable grippers longitudinally arranged next to one another.

13. The stent contracting apparatus of claim 12, wherein:
each row of retractable grippers are longitudinally placed along the outer tubular member, each row of retractable grippers being approximately 90 degrees apart from an adjacent row of retractable grippers.

14. The stent contracting appparatus for maintaining a self-expanding stent in a collapsed delivery position for implantation in a body lumen, comprising:
a plurality of retractable grippers moveable between a retracted position and a deployed position, each retractable gripper having a hook-like projection adapted to engage a strut on the stent to maintain the stent in a collapsed position when the retractable grippers are in the retracted position; and
means associated with each retractable gripper for moving the retractable gripper between the retracted and deployed positions, the retractable grippers being adapted to disengage from the struts of the stent when placed in the deployed position.

15. A system for delivering a self-expanding stent to an area of treatment, comprising:
an elongated tubular member having a proximal end and a distal end;
a stent contracting apparatus mounted near the distal end of the elongated tubular member including a plurality of retractable grippers moveable between a retracted position and a deployed position, each of the grippers having a hook-like projection adapted to engage a strut of the stent to maintain the stent in a collapsed position when the grippers are in their retracted position;
an actuating mechanism for moving the retractable grippers between the retracted and deployed positions, the grippers being adapted to disengage from the struts of the stent when placed in the deployed position;
an expandable member mounted on the tubular member for post expanding the stent in the area of treatment.

16. The stent delivery system of claim 15, wherein:
the expandable member is in fluid communication with a lumen which supplies inflation fluid for expanding the expandable member.

17. The stent contracting apparatus of claim 16, wherein:
the stent has a distal region and a proximal region and the retractable grippers progressively release the struts in the distal region of the stent for expansion prior to the release of the struts located in the proximal region of the stent.

18. The stent contracting apparatus of claim 15, wherein:
the retractable grippers progressively release the struts of the stent as the grippers are moved into the deployed position.

19. The stent contracting apparatus of claim 18, wherein:
each retractable gripper has a specific length and the retractable grippers are aligned such that the retractable grippers having a shorter length than an adjacent retractable gripper will disengage the strut of the stent prior to the longer adjacent retractable gripper.

20. The stent contracting apparatus of claim 15, wherein:
the actuating mechanism includes a plurality of actuating rails, each retractable gripper being pivotally mounted to one of the actuating rails, the actuating rails being moveable to move the retractable grippers between the retracted and deployed positions.

21. The stent contracting apparatus of claim 20, further including:
a housing for holding the plurality of retractable grippers and actuating rails, the housing including a plurality of apertures through which the hooklike projection of each retractable gripper extends radially outward therethrough.

22. The stent contracting apparatus of claim 21, wherein:
the housing is an outer tubular member having a distal end and a proximal end with a mounting disk located at each of the distal and proximal ends;
the retractable grippers being spaced longitudinally along the outer tubular member apart from one another to engage the struts of the stent when the grippers are placed in their retracted position, the mounting disks having openings extending therein for receiving the actuating rails which allow the actuating rails to move longitudinally along the length of the outer tubular member to move the retractable grippers between the retracted and deployed positions.

23. The stent contracting apparatus of claim 22, wherein:
each actuating rail is attached to a control wire which extends to a proximal location outside of the body lumen for selectively moving the rails longitudinally along the tubular member to move the retractable gripper between the retracted and deployed positions.

24. The stent contracting apparatus of claim 23, further including:

an inner tubular member having a proximal end and a distal end while the distal end, wherein the outer tubular member forming the housing is mounted coaxially over the inner tubular member near the distal end; and the inner tubular member has a lumen extending therethrough for receiving the control wires.

25. The stent contracting apparatus of claim 15, wherein:

the stent includes a plurality openings between the struts forming the stent and the hook-like projections of each retractable gripper is adapted to extend through an opening of the stent to engage the strut of the stent.

26. A method of delivering a self-expanding stent to an area of treatment region within a body lumen, comprising:

providing a stent delivery system which includes an elongated catheter body having a stent contracting apparatus on its distal extremity with retractable grippers having a hook-like projection for gripping a strut of the stent;

inserting the grippers through openings between the struts of the stent structure;

compressing the stent over the grippers to allow each hook-like projection to engage a strut of the stent structure;

retracting the grippers to hold the stent in a uniformly compressed low profile state;

advancing the stent delivery system through a body lumen until the stent contracting apparatus is disposed within the area of treatment;

releasing the grippers to cause the stent to expand within the area of treatment;

retracting the grippers sufficiently to remove the stent contracting apparatus from within the inner diameter of the expanded stent; and removing the delivery system from the body lumen.

27. The method of claim 26, wherein:

after the retraction of the grippers, the stent contracting apparatus is advanced through the inner diameter of the expanded stent until an expandable member mounted on the catheter body proximate to the stent contracting apparatus is disposed within the expanded stent and is inflated to adjust the positioning of the expanded stent in the area of treatment.

28. A method for delivery of a self-expanding stent to an area of treatment within a body lumen, comprising:

providing a stent delivery system including an elongated catheter body having a stent contracting device mounted on the distal extremity that includes a plurality of retractable grippers shiftable between a retracted and deployed position;

retracting the grippers to the retracted position and inserting the stent contracting device into the expanded stent;

deploying the grippers to engage and grip struts of the stent;

contracting the struts of the stent to a low profile collapsed contracted position and retracting the grippers to hold the struts of the stent in this low profile position;

advancing the catheter body with the stent contracting device into the body lumen to the area of treatment;

releasing the grippers to free the struts of the stent allowing the stent to expand outwardly in the area of treatment;

freeing the grippers from the stent and retracting the grippers from the stent; and removing the stent contracting device from the body lumen.

* * * * *